United States Patent [19]

Ritter et al.

[11] Patent Number: 5,198,574
[45] Date of Patent: Mar. 30, 1993

[54] PROCESS FOR THE IMPROVED PRODUCTION OF (METH)ACRYLIC ACID ESTERS OF POLYHYDRIC ALCOHOLS (II)

[75] Inventors: Wolfgang Ritter, Haan; Hans-Dieter Sitz, Rommerskirchen; Ludwig Speitkamp, Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 720,445

[22] PCT Filed: Dec. 15, 1989

[86] PCT No.: PCT/EP89/01550
  § 371 Date: Jun. 24, 1991
  § 102(e) Date: Jun. 24, 1991

[87] PCT Pub. No.: WO90/07487
  PCT Pub. Date: Jul. 12, 1990

[30] Foreign Application Priority Data

Dec. 24, 1988 [DE] Fed. Rep. of Germany ........ 3843938

[51] Int. Cl.$^5$ .................................................. C07C 69/52
[52] U.S. Cl. .................................................. 560/224
[58] Field of Search ........................................ 560/224

[56] References Cited

FOREIGN PATENT DOCUMENTS 331845 9/1989 European Pat. Off. .

OTHER PUBLICATIONS

CA 84(20):136272g 1975 [Jp Kokai 52142511 Nov. 17, 1975.

Primary Examiner—Paul J. Killos
Attorney, Agent, or Firm—Ernest G. Szoke; Wayne C. Jaeschke; Henry E. Millson, Jr.

[57] ABSTRACT

The invention relates to a process for the production of (meth)acrylic acid esters of polyhydric alcohols by reaction thereof with acrylic acid and/or methacrylic acid in the presence of acidic esterification catalysts with addition of polymerization inhibitors to the reaction mixture. The new process is characterized in that, where unsubstituted phenolic compounds are used as inhibitors, the esterification reaction is carried out with addition of active carbon to the reaction mixture. The preferred inhibitor is hydroquinone. In addition, the esterification reaction is preferably carried out in the absence of liquid solvents and/or azeotropic entraining agents.

22 Claims, No Drawings

PROCESS FOR THE IMPROVED PRODUCTION OF (METH)ACRYLIC ACID ESTERS OF POLYHYDRIC ALCOHOLS (II)

This invention relates to a process for the production of polyfunctional esters of acrylic acid and/or methacrylic acid—hereinafter referred to as (meth)acrylic acid esters or poly(meth)acrylic acid esters—with polyhydric alcohols by reaction of the reactants in the presence of acidic esterification catalysts with addition of polymerization inhibitors to the reaction mixture.

(Meth)acrylic acid esters of polyhydric alcohols, particularly from the group of dihydric to tetrahydric aliphatic saturated alcohols and their alkoxylation products, are being used to an increasing extent as highly reactive constituents in radiation-curing systems. Polyfunctional (meth)acrylic acid esters of the type in question may be used, for example, as paint constituents for hardening by electron beams or as a constituent of UV-hardening printing inks or corresponding paints, surfacing, molding or encapsulating compounds or even in adhesives, particularly anaerobic adhesives. However, their production is not without problems. The end products are required in particular to be colorless with a low acid value, high stability in storage and hardly any odor. (Meth)acrylic acid esters of the type in question generally cannot be purified by distillation on account of their high molecular weight and their high reactivity. Accordingly, the products are intended to accumulate directly as colorless products of the esterification reaction. The esterification reaction requires the presence of highly effective inhibitors which, in turn, should not initiate any unwanted secondary reactions, for example in the form of discoloration.

Extensive literature is available on the production of such polyfunctional (meth)acrylic acid esters of polyhydric alcohols, cf. in particular DE-OS 29 13 218 and the relevant literature cited therein. Thus, it is known from DE-AS 12 67 547 and from the Journal "Chem. and Ind." 18 (1970), 597, that polyfunctional (meth)acrylic acid esters can be produced by azeotropic esterification of (meth)acrylic acid with polyhydric alcohols in the presence of azeotropic entraining agents and also acidic catalysts and polymerization inhibitors, such as phenols, phenol derivatives, copper, copper compounds or phenothiazine. Organic or inorganic acids or acidic ion exchangers are used as the acidic catalysts, p-toluene sulfonic acid and sulfuric acid being preferred. The esterification reaction takes place in particular at temperatures in the range from 40° to 120° C. Suitable azeotropic entraining agents for removing the water of reaction are aliphatic or cycloaliphatic or aromatic hydrocarbons or mixtures thereof having boiling ranges within the stated temperature limits.

It is proposed in DE-OS 29 13 218 cited above to carry out the azeotropic esterification in the presence of at least one organic ester of phosphorous acid in addition to a phenol-based inhibitor. However, the reaction again has to be carried out in the presence of at least one aliphatic, cycloaliphatic and/or aromatic hydrocarbon boiling at 40° to 120° C. The water of reaction formed is said to be azeotropically removed from the reactor by this entraining agent. According to the Examples of this publication, the reaction time is put at 10 to 18 hours.

The problem addressed by the invention is to establish reaction conditions for the esterification reaction in question which, on the one hand, enable the reaction time to be considerably shortened but which, on the other hand, do not adversely affect the quality of the esterification products formed, particularly their high color quality. In addition, the invention seeks to eliminate the need for comparatively complex inhibitor systems of the type described in DE-OS 29 13 218 cited above. Another problem addressed by the invention is to enable the application inhibitor required in practice for the highly reactive systems in question to be used simultaneously as a reaction inhibitor in the synthesis of the polyfunctional (meth)acrylic acid esters.

The teaching according to the invention is concerned in particular with the problems which arise in reactions of the described type when unsubstituted phenolic compounds, particularly hydroquinone, are used as sole inhibitor or at least as the principal inhibitor component. The use of hydroquinone as a polymerization inhibitor in practice may be desirable from the application standpoint. When used as a reaction inhibitor, hydroquinone causes problems, particularly in regard to the color of the reaction product form. The mere treatment of such highly discolored reaction products with, for example, active carbon as a decolorizing agent does not have the required lightening effect. Nevertheless, it has surprisingly been found that effective relief in this regard can be provided by following the teaching according to the invention as described hereinafter.

In one preferred embodiment, the technical solution provided by the invention is based on the observation that that esterification products of comparatively high purity can be directly obtained as end products of the process, even in the absence of diluents or azeotropic entraining agents, and that it is even possible under the solventless reaction conditions to apply comparatively relatively drastic esterification conditions which enable the reaction time to be considerably shortened. To this end, it is necessary in particular to carry out the process under the conditions described hereinafter.

Accordingly, the present invention relates to a process for the production of (meth)acrylic acid esters of polyhydric alcohols by reaction thereof with acrylic acid and/or methacrylic acid in the presence of acidic esterification catalysts with addition of polymerization inhibitors to the reaction mixture. The new process is characterized in that, where phenolic compounds unsubstituted in the α-position are used as inhibitors, the esterification reaction is carried out with addition of active carbon to the reaction mixture. The preferred phenol-based inhibitor unsubstituted in the α-position is hydroquinone.

It has surprisingly been found that the use of active carbon during the actual condensation reaction—and not in a subsequent reaction step—effectively prevents the formation of undesirably heavily discolored reaction products. The amount of active carbon used may be selected within wide limits and is preferably several times the quantity of the phenolic compound, i.e. above all hydroquinone, used as inhibitor. Although the color of the reaction product can be satisfactorily lightened with 2 to 10 times the quantity of active carbon, the active carbon is nevertheless generally used in even larger quantities, for example of 10 to 100 times and preferably about 20 to 60 times the quantity of hydroquinone. It had not been expected that the use of such comparatively large quantities of active carbon would leave the inhibitor effect against unwanted premature polymerization substantially unimpaired. The known adsorptivity of the large surface of the active carbon evidently acts mainly against colored impurities formed during the reaction, removing them substantially selectively from the reaction mixture without, at the same time, impairing the effect of the phenolic compounds used basically in only small quantities as polymerization inhibitor.

In another important and preferred embodiment of the invention, the reaction mixtures used are liquid at room temperature and are at least substantially free from solvents and/or azeotropic entraining agents. In this embodiment of the invention, there is no need at all for such auxiliaries which . . . the course of the reaction and, hence, basically reduce unwanted discoloration. Where this procedure is adopted, the water of condensation formed is best removed from the gas phase of the reaction zone.

In another preferred embodiment of the invention, the reaction zone is purged with a gas stream and the gas stream in question is used in particular to remove the water of condensation formed during the esterification reaction from the reactor. It is preferred to use a gas stream which contains a limited amount of free oxygen. Depending on the particular process conditions selected, air or an oxygen-depleted gas mixture, for example a nitrogen/air mixture, may be used as the gas stream. In general, however, a certain content of free oxygen will be desirable in this gas phase delivered to the reaction mixture. These limited quantities of oxygen activate the inhibitor in known manner during the course of the reaction.

The oxygen content of the gas mixture is generally at least of the order of 1% by volume and preferably in the range from about 2 to 20% by volume. In the interests of reaction safety, the free oxygen contents are preferably in the lower half of this range, i.e. up to about 10% by volume and preferably up to about 7% by volume. In one preferred embodiment of the invention, the gas stream is fed into the liquid reaction mixture and can bubble through it, for example in finely divided form. It is best to use limited quantities of this gas stream so that there is no undesirably high discharge of reaction components, particularly the comparatively low-volatility acids.

On completion of the esterification reaction, the active carbon is removed from the reaction mixture. This may be done in particular by filtration. It is possible in this way to produce high-purity and, in particular, substantially colorless radiation-curable polyfunctional (meth)acrylic acid esters, even under the comparatively drastic reaction conditions selected for the process according to the invention. In addition, the polyfunctional (meth)acrylic acid esters readily obtained are distinguished by high stability in storage.

The polymerization inhibitor or, optionally, the inhibitor mixture is typically added to the reaction mixture in quantities of from 200 to 10,000 ppm and preferably in quantities of from about 300 to 2,000 ppm, based in each case on the weight of the reaction mixture of (meth)acrylic acid and polyhydric alcohols.

Suitable polyalcohols for esterification are, for example, ethylene glycol, propylene glycol, butane-1,4-diol, hexane-1,6-diol, neopentyl glycol, diethylene glycol, triethylene glycol, dimethylol propane, glycerol, trimethylol propane, trimethylol hexane, trimethylol ethane, hexane-1,3,5-triol and pentaerythritol. According to the invention, however, particularly suitable polyhydric alcohols are also the alkoxylation products of the above-mentioned polyhydric alcohols, particular significance being attributed in this regard to the ethoxylation products and/or propoxylation products. Chain-extended polyhydric alcohols of this type may contain considerable quantities of polyalkoxide groups, for example 1 to 50 mol and preferably about 1 to 20 mol ethylene oxide per g-equivalent hydroxyl groups.

Suitable esterification catalysts for the process according to the invention are commercially available organic or inorganic acids or even acidic ion exchangers, particular significance being attributed to the corresponding compounds frequently used in practice, namely p-toluene sulfonic acid and sulfuric acid. The esterification catalyst is used in quantities of, for example, from 0.1 to 5% by weight, based on the esterification mixture.

The reactants are preferably reacted at sump temperatures of at least about 90° C. and, preferably, of at least about 100° C., the temperature range up to about 150° C. being particularly suitable. The reaction may be carried out under normal pressure, although it is best carried out under reduced pressure. Where the reaction is carried out under reduced pressure, it is possible in one particular embodiment to reduce the pressure towards lower pressures either in steps or continuously.

Through the possibility of working under comparatively drastic esterification conditions and, at the same time, reduced pressure, the reaction time is considerably shortened by comparison with hitherto known processes. Thus, yields of at least 90% of the theoretical and, preferably, of at least around 94% of the theoretical may be obtained in the process according to the invention for a reaction time of no more than about 10 hours and, preferably, of no more than about 8 hours at temperatures in the range from about 100° to 140° C. Nevertheless, the reaction products are obtained in the form of a stabilized mass which is light in color or may be effectively purified by a simple aftertreatment.

The crude reaction product containing the acidic esterification catalyst is subsequently subjected to neutralization. This neutralization step may be carried out under known wet conditions, for example by the use of aqueous solutions containing soda and, optionally, sodium chloride. In one preferred embodiment, however, the crude reaction product containing the acidic catalyst is subjected to dry neutralization. Suitable dry neutralizing agents are the oxides and/or hydroxides of the alkali metals, the alkaline earth metals and/or aluminium. Corresponding compounds of magnesium or calcium are particularly suitable for the dry neutralization.

(Meth)acrylic acid and the alcohols may be used in equivalent quantities for the esterification reaction. However, where more than dihydric alcohols are used, it is readily possible only partly to esterify the hydroxyl groups. For full esterification, it may be best to use the acid component in a slight excess over the stoichiometric quantity required for esterification of the hydroxyl groups. This slight excess may amount to at least about 10 mol-%. If desired, an inhibitor may be additionally incorporated in the reaction product on completion of the reaction.

Should slight discoloration of the reaction product occur after all during production under the drastic esterification conditions according to the invention, it may readily be eliminated by an aftertreatment with decolorizing agents. Aluminium oxide, for example, is a suitable decolorizing agent.

EXAMPLES

Example 1

928.8 g acrylic acid, 1560.4 g of a propoxylated neopentyl glycol (OH value 460 mg KOH/g substance), 87.1 g p-toluene sulfonic acid and 124.5 g (5%, based on acrylic acid+polyol) active carbon were weighed into a 3 liter reactor and inhibited with 2.5 g hydroquinone (1100 ppm, based on the quantity of product). An air/nitrogen mixture (5% by volume $O_2$; 20 l/h) was passed through the reaction mixture during the esterification reaction and water was removed. For a constant bath temperature of 143° C. and a maximum sump temperature of 135° C., the esterification time was 5 hours. The mixture was cooled and the active carbon was filtered off in a pressure nutsche.

Crude product:
Acid value: 34 mg KOH/g
OH value: 10 mg KOH/g
Yield: 96.7%
Gardner color standard number: <1
Viscosity: 92 mPas The crude product was washed with 4 liters aqueous 16% by weight NaCl/4% by weight $NaHCO_3$ solution, reinhibited with 200 ppm hydroquinone monomethyl ether, dried in vacuo for 3 hours at 80° C./4 mbar and then filtered in a pressure nutsche.
Product:
Acid value: <1 mg KOH/g
OH value: <15 mg KOH/g
Gardner color standard number: 3

Comparison Example 1

The procedure was as in Example 1, except that no active carbon was added.
Crude product:
Acid value: 39 mg KOH/g
OH value: <15 mg KOH/g
Yield: 97.1%
Gardner color standard number: 12
Viscosity: 90 mPa.s The crude product was worked up as in Example 1.
Product:
Acid value: <1 mg KOH/g
OH value: <15 mg KOH/g
Gardner color standard number: 8-9.

Example 2

The procedure was as in Example 1, except that the active carbon was reduced from 124.5 to 24.9 g (1%, based on acrylic acid+polyol).
Crude product:
Acid value: 30 mg KOH/g
OH value: <15 mg KOH/g
Yield: 97.3%
Gardner color standard number: 6-7

The crude product was worked up as in Example 1.
Product:
Acid value: <1 mg KOH/g
OH value: <15 mg KOH/g
Gardner color standard number: 5-6.

TABLE 1

Dependence of the Gardner color standard number on the quantity of active carbon at different hydroquinone concentrations in the esterification of acrylic acid with propoxylated neopentyl glycol

| Quantity of A carbon x-fold excess, based on hydroquinone | Gardner color standard number of the crude product with hydroquinone | |
| --- | --- | --- |
| | 500 ppm | 1000 ppm |
| 100 | <1 | — |
| 80 | <1 | — |
| 60 | <1 | — |
| 50 | — | <1 |
| 40 | 1-2 | <1 |
| 30 | — | 1-2 |
| 20 | 5 | 5 |
| 10 | — | 6-7 |
| 0 | 12 | 12 |

Example 3

1198.8 g acrylic acid, 1362.3 g of an ethoxylated trimethylol propane (OH value 680 mg KOH/g substance), 89.6 g p-toluene sulfonic acid, 128.1 g (5% by weight, based on acrylic acid+polyol) active carbon and 2.56 g hydroquinone (1100 ppm, based on the quantity of product) were weighed into a 3 liter reactor.

An air/nitrogen mixture (5% by volume $O_2$; 20 l/h) was passed through the reaction mixture during the esterification reaction and water was removed. For a constant bath temperature of 143° C. and a maximum sump temperature of 135° C., the esterification time was 5 hours. The mixture was cooled and the active carbon was filtered off in a pressure nutsche.
Crude product:
Acid value: 25.3 mg KOH/g
OH value: 12 mg KOH/g
Yield: 96.3%
Gardner color standard number: 3
Viscosity: 78.9 mPas The crude product was washed with 4 liters aqueous 16% by weight NaCl/4% by weight $NaHCO_3$ solution, inhibited with 200 ppm hydroquinone monomethyl ether, dried in vacuo for 3 hours at 80° C./40 mbar and then filtered in a pressure nutsche.
Product:
Acid value: <1 mg KOH/g
OH value: <15 mg KOH/g
Gardner color standard number: 4

Comparison Example 2

The procedure was as in Example 3, except that no active carbon was added.
Crude product:
Acid value: 27 mg KOH/g
OH value: <15 mg KOH/g
Yield: 96.4%
Gardner color standard number: 11-12

The crude product was worked up as in Example 3.
Product:
Acid value: <1 mg KOH/g
OH value: <15 g KOH/g
Gardner color standard number: 7.

Example 4

The procedure was as in Example 3, except that the active carbon was reduced from 128.1 g to 25.6 g (1% by weight, based on acrylic acid+polyol).
Crude product:

Acid value: 28.3 mg KOH/g
OH value: <15 mg KOH/g
Yield: 95.4%
Gardner color standard number: 8

The crude product was worked up as in Example 3.
Product:
Acid value: <1 mg KOH/g
OH value: <15 mg KOH/g
Gardner color standard number: 6-7.

TABLE 2

Dependence of the Gardner color standard number on the quantity of active carbon at different hydroquinone concentrations in the esterification of acrylic acid with ethoxylated trimethylol propane

| Quantity of A carbon x-fold excess, based on hydroquinone | Gardner color standard number of the crude product with hydroquinone | |
|---|---|---|
| | 500 ppm | 1000 ppm |
| 100 | 2 | — |
| 80 | 2 | — |
| 60 | 3 | — |
| 50 | — | 3 |
| 40 | 5 | 3 |
| 30 | — | 3-4 |
| 20 | 8 | 6-7 |
| 10 | — | 8 |
| 0 | 11-12 | 11-12 |

We claim:

1. In a process for the production of (meth)acrylic acid esters of polyhydric alcohols by reaction of at least one polyhydric alcohol with acrylic acid and/or methacrylic acid in the presence of an acidic esterification catalyst and a polymerization inhibitor in the reaction mixture, the improvement comprising
   A. the use of at least one α-unsubstituted phenolic compound as the polymerization inhibitor, and
   B. the addition of active carbon to the reaction mixture.

2. The process of claim 1 wherein the quantity by weight of active carbon added to the reaction mixture is at least several times that of the at least one α-unsubstituted phenolic compound.

3. The process of claim 2 wherein from about 10 to about 100 times as much active carbon is added.

4. The process of claim 2 wherein from about 20 to about 60 times as much active carbon is added.

5. The process of claim 1 wherein the reaction mixture is liquid at room temperature and is at least substantially free from solvents and azeotropic entraining agents.

6. The process of claim 1 wherein the water of condensation formed in the reaction is removed from the gas phase of the reaction zone.

7. The process of claim 1 wherein the reaction zone is purged with a gas stream containing free oxygen.

8. The process of claim 7 wherein air or a nitrogen/air mixture is used as the gas stream.

9. The process of claim 1 wherein the reaction is carried out at a sump temperature in the range of from about 90° to about 150° C.

10. The process of claim 9 wherein said temperature is from about 100° to about 140° C.

11. The process of claim 1 wherein the reaction is carried out at a subatmospheric pressure.

12. The process of claim 1 wherein the α-unsubstituted phenolic compound is hydroquinone.

13. The process of claim 1 wherein the at least one α-unsubstituted phenolic compound is present in from about 200 to about 10,000 ppm, based on the weight of the reaction mixture.

14. The process of claim 13 wherein from about 300 to about 2,000 ppm of phenolic compound is present.

15. The process of claim 1 wherein the reaction is carried out to a yield of product of at least 90% based on theoretical, but wherein the reaction time is not greater than about 10 hours.

16. The process of claim 1 wherein the reaction product is subjected to dry neutralization.

17. The process of claim 16 wherein the dry neutralization is carried out with at least one oxide or hydroxide of an alkali metal, an alkaline earth metal, or aluminum.

18. The process of claim 1 wherein the reaction product is treated with a decolorizing agent.

19. The process of claim 1 wherein the quantity by weight of active carbon added to the reaction mixture is at least several times that of the at least one α-unsubstituted phenolic compound; the reaction mixture is liquid at room temperature and is at least substantially free from solvents and azeotropic entraining agents; the water of condensation formed in the reaction is removed from the gas phase of the reaction zone; the reaction zone is purged with a gas stream containing free oxygen; and the reaction is carried out at a sump temperature in the range of from about 90° to about 150° C.

20. The process of claim 19 wherein the reaction is carried out at subatmospheric pressure.

21. The process of claim 19 wherein the reaction temperature is from about 100° to about 140° C.; the quantity of active carbon is from about 10 to about 100 times that of the at least one α-unsubstituted phenolic compound; the at least one α-unsubstituted phenolic compound is present in from about 200 to about 10,000 ppm, based on the weight of the reaction mixture; and the reaction is carried out to a yield of product of at least 90% based on theoretical, but wherein the reaction time is not greater than about 10 hours.

22. The process of claim 21 wherein from about 300 to about 2,000 ppm of phenolic compound is present; air or a nitrogen/air mixture is used as the gas stream; and the reaction product is subjected to dry neutralization.

* * * * *